(12) United States Patent
Moss et al.

(10) Patent No.: US 10,779,510 B1
(45) Date of Patent: Sep. 22, 2020

(54) ANIMAL HEALTH MONITORING DEVICE AND SYSTEM

(71) Applicant: Animal Health Analytics, Inc., Gulf Shores, AL (US)

(72) Inventors: Harrison Moss, Gulf Shores, AL (US); Terry Brandebourg, Auburn, AL (US)

(73) Assignee: Animal Health Analytics, Inc., Gulf Shores, AL (US)

( * ) Notice: Subject to any disclaimer, the term of this patent is extended or adjusted under 35 U.S.C. 154(b) by 425 days.

(21) Appl. No.: 15/726,667

(22) Filed: Oct. 6, 2017

(51) Int. Cl.
| | | |
|---|---|---|
| A01K 11/00 | (2006.01) | |
| A01K 29/00 | (2006.01) | |
| A61B 5/06 | (2006.01) | |
| A61B 5/0205 | (2006.01) | |
| A61B 5/01 | (2006.01) | |

(52) U.S. Cl.
CPC .......... *A01K 11/001* (2013.01); *A01K 11/006* (2013.01); *A01K 29/005* (2013.01); *A61B 5/01* (2013.01); *A61B 5/0205* (2013.01); *A61B 5/067* (2013.01)

(58) Field of Classification Search
CPC .. A01K 11/001; A01K 11/006; A01K 11/004; A01K 11/005; A61B 5/01; A61B 5/0205; A61B 5/067; G01K 1/02; G01K 13/00; G01K 23/00

USPC .......... 119/858; 24/705, 704.1, 707.1, 703.1, 24/703.3, 703.4, 454, 331, 332, 338
See application file for complete search history.

(56) References Cited

U.S. PATENT DOCUMENTS

| | | | | |
|---|---|---|---|---|
| 4,435,880 | A * | 3/1984 | Gardner | A44B 6/00 24/332 |
| 9,848,577 | B1 * | 12/2017 | Brandao | A01K 15/023 |
| 2002/0010390 | A1 * | 1/2002 | Guice | A61B 5/0031 600/300 |
| 2016/0120628 | A1 * | 5/2016 | Kapil | A61M 37/00 604/22 |
| 2018/0333244 | A1 * | 11/2018 | Hanks | A01K 29/005 |
| 2020/0178800 | A1 * | 6/2020 | Geissler | A61B 5/01 |

* cited by examiner

*Primary Examiner* — Ebony E Evans
(74) *Attorney, Agent, or Firm* — ADAMSIP, LLC; Stephen Thompson; J. Hunter Adams

(57) ABSTRACT

A device, system, and method for remotely monitoring animal health is provided. The device is secured to an ear of an animal to be monitored and has a sensor that obtains animal health data. The ear is positioned between a sensor housing and a disc, which are both secured to a post inserted through an opening in the ear. The device includes a spring that causes the disc to be biased toward the ear in order to maintain a snug fit to obtain consistent and accurate reading from the heart rate sensor. The spring allows for animal growth so that the device may be fitted to a young animal and may remain in place for the duration of the life of the animal.

23 Claims, 4 Drawing Sheets

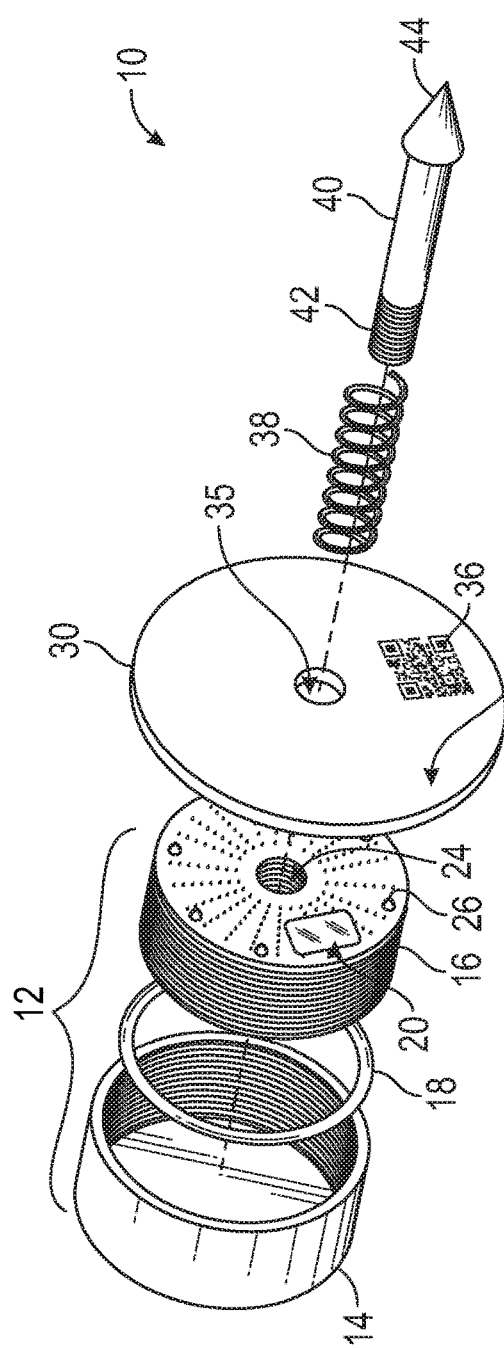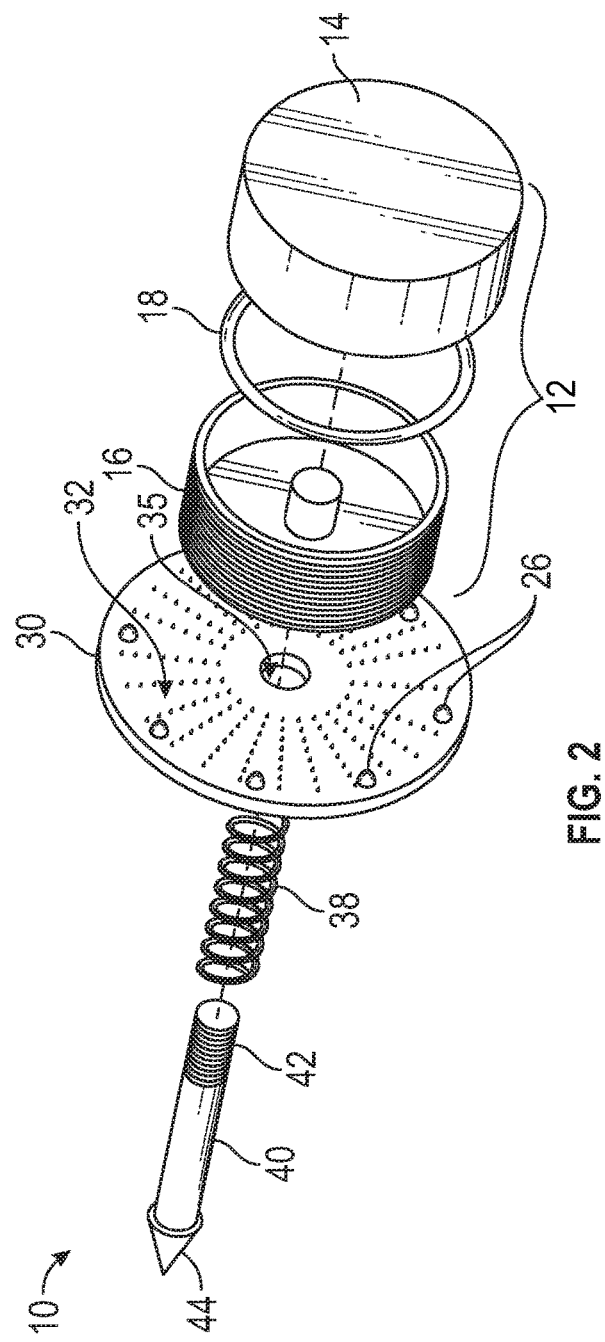

ANIMAL HEALTH MONITORING DEVICE AND SYSTEM

FIELD OF THE INVENTION

The present invention relates generally to a health monitoring device and system for use with animals.

BACKGROUND

Most pork produced in the United States is produced on large farms. Due to consolidation in the pork industry in recent years, over 90% of the annual pig crop is produced on operations with at least 5,000 head. There are many challenges in maintaining healthy animals on such large farms. A variety of health conditions may arise in an animal population such as dehydration, lameness, or other illnesses. For instance, heather parameter indicators such as dehydration and stress can result in up to 15% mortality in a herd annually. Finding and treating pigs displaying symptoms of dehydration, stress, or other health conditions presents serious challenges on a large farm. Some of the symptoms of dehydration may include lack of appetite, lack of coordination, nose or ear twitching, paddling movements, and increase in body temperature. In some cases, a pig may stand or "dog sit", sometimes pressing the animal's head against a wall. In some cases, death in pigs may result in as little as 1-2 hours after the first appearance of symptoms. In cases where dehydration is the result of a water restriction, a large number of animals may be affected and symptoms may not appear until after the water supply has been restored. Provided that a dehydrated pig can be slowly re-hydrated, many will recover over a 24-48 hour time period.

Current methods to monitor the health parameters of pigs or other commercially-raised farm animals include visual inspection or video surveillance of animals. However, visually identifying and manually picking out individual animals in crowded pens is a time-consuming and ineffective method for identifying and treating animals showing signs of dehydration or other health problems. Environmental controls may be utilized in an animal enclosure to minimize health problems for animals housed in the enclosure, but these controls do not monitor individual animals and thus are ineffective in early identification and diagnosis of animals requiring treatment for dehydration or other conditions. In addition, visual inspection is also the method generally used to determine when a sow is in estrus. However, this method requires frequent inspection and may be ineffective in determining the most advantageous insemination time for the sow.

Some remote monitoring systems have been developed in recent years to remotely provide some information regarding the condition and health paramters of individual animals. Known systems may utilize tags attached to the ear of an animal to obtain information about the animal. However, such systems generally provide a limited amount of information, such as information relating to body temperature, animal mobility, and rumination in the case of ruminating animals such as cows. This information may be limited in scope due to the types of known tags utilized, which are generally not capable of effectively providing certain types of health information. Thus, the information provided about individual animals may be of limited usefulness in terms of timely identification and treatment of animals for certain conditions such as dehydration, which is of particular concern with respect to certain types of farm-raised animals such as pigs. In addition, currently available tags do not account for animal growth in the design of the tag. Thus, known tags may not produce consistent health data when fitted to a young animal experiencing rapid growth.

Accordingly, a need exists in the art for an animal health monitoring device and system that can remotely and effectively monitor the health of individual animals without the necessity of regular visual inspection or surveillance of animals. Furthermore, a need exists in the art for an animal health monitoring device adapted to accommodate animal grown while providing consistent health data throughout the life of the animal.

SUMMARY

In one aspect, a device for remotely monitoring animal health is provided. The device is configured such that the device may be secured to an ear of an animal to be monitored. The device is further configured to collect data about the health of the animal from the animal's ear via a sensor. The health data and parameters relating to the animals are then wirelessly transmitted to a remote monitor so that a user may remotely monitor the health of the animal. Various types of animal health data may be collected which may be used to directly monitor the health of the animal or may be used indirectly as inputs in calculating a metric related to animal health, such as a hydration level of the animal.

The device comprises a sensor housing and a post attached to the sensor housing at a first end of the post. The post extends outwardly from the sensor housing and has an end cap having a diameter larger than a diameter of the post. The cap is preferably pointed and integrally attached to the post. The device further comprises a disc having an opening extending through the disc and sized to receive the post therethrough so that the disc is slidably secured to the post. The device additionally comprises a spring positioned around the post and disposed between the disc and the cap such that the disc is biased toward the first end of the post. When the device is fitted to an animal, the post extends through an opening in the ear of the animal, and the ear fits between the first end of the post and the disc such that one side of the ear contacts an inner facing surface of the sensor housing and an opposite side of the ear contacts an inner facing surface of the disc. In a preferred embodiment, the inner facing surfaces are textured surfaces and may additionally have bumps spaced throughout the inner facing surfaces that are larger than relatively small projections that form the textured surface surrounding the bumps.

In one embodiment, the sensor house supports a temperature gauge positioned near the ear of the animal. The temperature gauge is preferably a digital gauge. The embodiment may include a heart rate sensor positioned to measure a heart rate of the animal. The heart rate sensor is preferably an electro-optical heart rate sensor that shines light on the skin of the animal's ear to detect changes in blood flow that occur with each heartbeat. The sensor housing has a transparent window positioned directly adjacent to the ear of the animal through which the sensor shines light to detect heart rate. When the device is secured to the ear of an animal, the spring causes the disc to be biased toward the animal's ear, thereby ensuring a snug fit to the ear at all times. As the animal grows and the ear becomes thicker, the spring may become more compressed, thereby maintaining the snug fit. This feature is particularly advantageous when fitting the device to a young animal. For instance, the device may be fitted to a newborn piglet and may remain in place on the ear of the pig until the stage of slaughter, which typically occurs around an animal weight of 270 pounds. Because the average daily gain of a pig is typically at least 1.5 pounds per day over an approximate life span of 165 days, the rapid growth experienced by pigs may cause the thickness of the ear to change significantly over the life span. The post and the spring of the device are sized and adapted to accommodate such growth without requiring changing or adjusting the device.

In addition, the textured surfaces and bumps on the inner facing surfaces of the device prevent the device from rotating when fitted onto the ear, which maintains the position of the window relative to a desired position on the ear, which is preferably adjacent to an auricular vein. The textured surfaces may also keep the temperature sensor in a preferred location on the animal's ear. Thus, this feature in combination with the spring keep the inner facing surfaces of the disc and the sensor housing in direct contact with the ear and also maintain proper positioning on the ear so that the device may obtain consistent, accurate temperature or heart rate readings.

The sensor is preferably configured to also function as a thermometer and an oximeter. In addition, the device preferably further comprises an accelerometer. Thus, data relating to heart rate, temperature, oxygen saturation in the blood, and motion may be used in calculating a metric related to animal health, such as a hydration level of the animal.

In another aspect, a system for remotely monitoring animal health of a plurality of animals is provided. The system comprises a plurality of monitoring devices each fitted onto the ear of an individual animal, at least one aggregator, and a remote monitor configured to wirelessly receive and display data related to specific individual animals within a group. Preferably, a plurality of aggregators are positioned around a pen, barn, or similar type of animal enclosure and aggregate data received from the plurality of devices fitted onto the animals within the enclosure. The aggregators are connected to a network to which a remote monitor is connected so that a user may remotely monitor the health of all animals fitted with monitoring devices.

The remote monitor may be used to observe data relating to individual animals and recorded and/or calculated at defined time intervals. The data may include heart rate data, temperature data, oxygen saturation data, motion data, and/or hydration data. The data is tracked over time so that trends may be observed. In a preferred embodiment, the system further comprises an alert system adapted to alert a user when a defined health parameter of an individual animal falls outside predefined limits. The user may receive an alert on a smartphone, personal computer, or tablet by an email, text message, or similar type of notification method. In a preferred embodiment, each device fitted onto an animal further comprises an alert light that is activated when the user receives an alert regarding an individual animal. The light allows the user to easily identify the animal requiring attention when the animal is in a large group.

Preferably, the disc of each device has an outer surface displaying a barcode that is linked to secondary data related to the specific individual animal to which the device is fitted. For instance, the barcode may be linked to data relating to genetic information of the animal, vaccination history, illness history, feed history, and/or barn, crate, or pen history. Thus, a user may select an individual animal from a list of all animals in the system and observe such secondary data about the animal. In addition, the system may be configured to provide alerts to the user based on secondary data. For instance, if the animal needs a vaccination or a follow-up inspection at a certain time, a notification may be sent to the user.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DESCRIPTION OF THE DRAWINGS

These and other features, aspects, and advantages of the present invention will become better understood with regard to the following description, appended claims, and accompanying drawings where:

FIG. 1 shows an exploded view of a device for remotely monitoring the health of an animal in accordance with the present disclosure.

FIG. 2 shows an exploded view of a device for remotely monitoring the health of an animal in accordance with the present disclosure.

DETAILED DESCRIPTION

In the Summary above and in this Detailed Description, and the claims below, and in the accompanying drawings, reference is made to particular features, including method steps, of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term "comprises" and grammatical equivalents thereof are used herein to mean that other components, ingredients, steps, etc. are optionally present. For example, an article "comprising" components A, B, and C can contain only components A, B, and C, or can contain not only components A, B, and C, but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Figure 3:
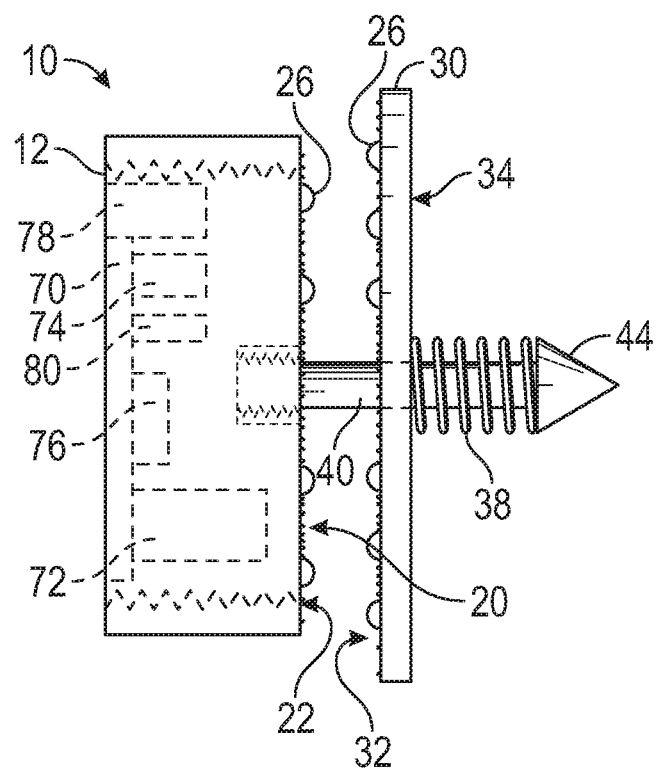
FIG. 3 shows a side elevational view of a device for remotely monitoring the health of an animal in accordance with the present disclosure.
Figure 5:
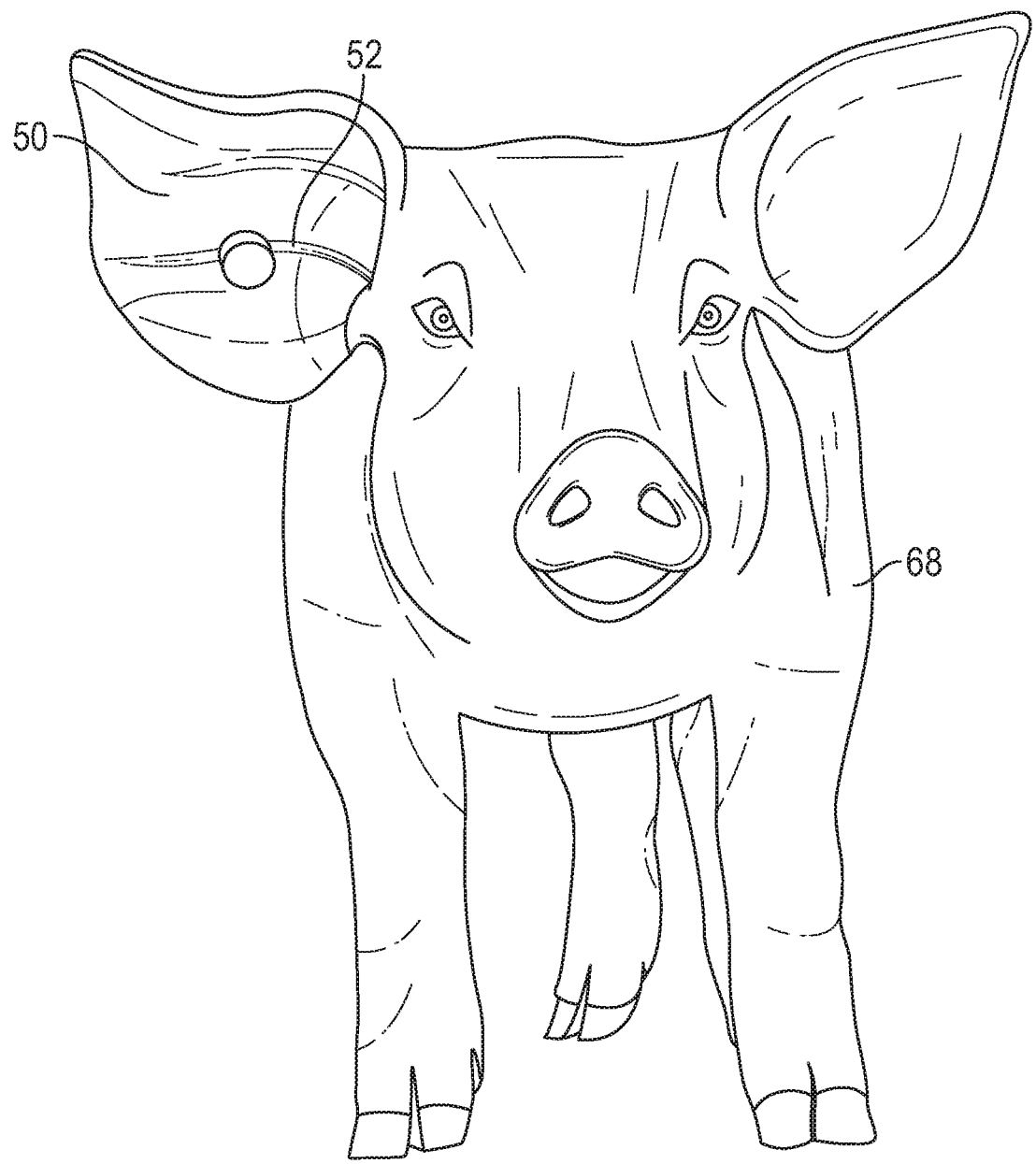
FIG. 5 shows a perspective view of a device for remotely monitoring the health of an animal fitted to an ear of a pig in accordance with the present disclosure.
Figure 6:
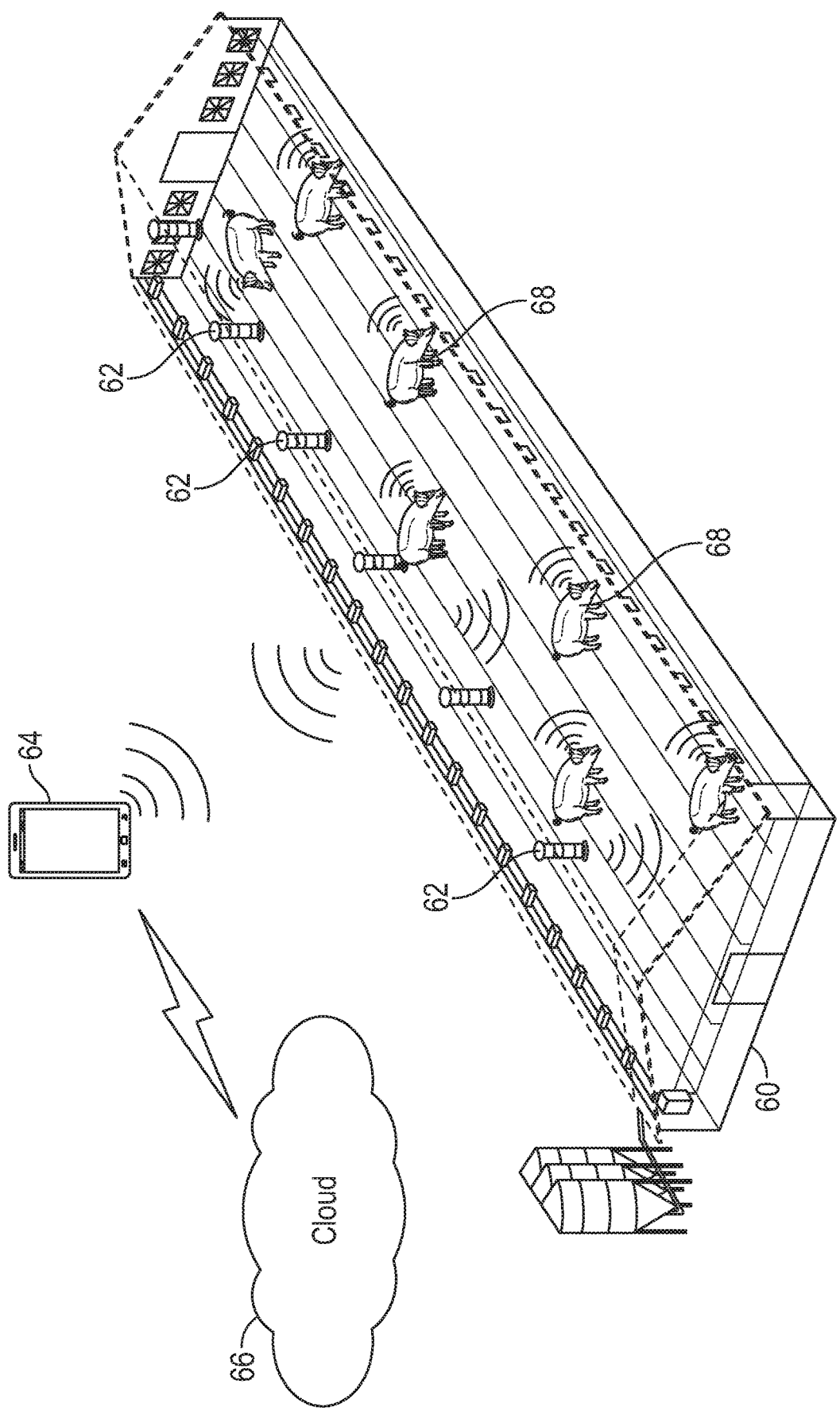
FIG. 6 shows a perspective view of a system for remotely monitoring animal health in accordance with the present disclosure.

Turning now to the drawings, FIGS. 1-3 illustrate a device 10 for remotely monitoring animal health parameters such as temperature, heart rate, activity, feeding and drinking habits, perspiration, and the like. The device 10 is configured such that the device may be secured to an ear 50 of an animal 68 to be monitored, as shown in FIG. 5. The device 10 is further configured to collect data about the health of the animal 68 from the animal's ear 50 via a sensor 72. The health data relating to the animals is then wirelessly transmitted to a remote monitor 64 so that a user may remotely monitor the health of the animal. As shown in FIG. 6, data may be first transmitted to one or more aggregators 62 that are connected to the monitor 64 via a network.

The device 10 comprises a sensor housing 12 that provides support for components of the device 10 including the sensor 72 and a battery 78 for powering the device. In a preferred embodiment, as shown in FIGS. 1 and 2, the sensor housing 12 comprises an outer case 14 having female threads and an inner case 16 having male threads so that the inner case 16 can be threaded into the outer case 14 to form the sensor housing 12. The interior of the sensor housing 12 is hollow so that the housing 12 can contain and support various components of the device 10 inside the housing 12. Preferably, a rubber or plastic O-ring 18 is included in the sensor housing 12 and fits around the inside of a circular base of the outer case 14 when the inner case 16 is threaded onto the outer case 14. The O-ring 18 prevents environmental moisture from entering the interior of the housing 12.

The device 10 further comprises a post 40 secured to the sensor housing 12 at a first end of the post 40. In a preferred embodiment, the first end of the post has male threads 42 so that the post 40 may be secured to the sensor housing 12 by threading the male threads 42 into a hole 24 in the inner case 16 having female threads, as shown in FIG. 1. Once secured to the sensor housing 12, the post 40 extends outwardly from the housing 12 and has an end cap 44 secured to an opposing second end of the post 40. The cap 44 has a diameter larger than a diameter of the post 12. The cap 44 is preferably pointed and integrally attached to the post 40. The device 10 further comprises a disc 30 having an opening 35 extending through the disc 30 and sized to receive the post 40 therethrough so that the disc 30 is slidably secured to the post 40. As shown in FIG. 1, the disc 30 is preferably generally round and the opening 35 is located at the center of the disc 30. The device 10 additionally comprises a spring 38 positioned around the post 40 and disposed between the disc 30 and the cap 44, as shown in FIG. 3, such that the disc 30 is biased toward the first end of the post 40.

Figure 4:
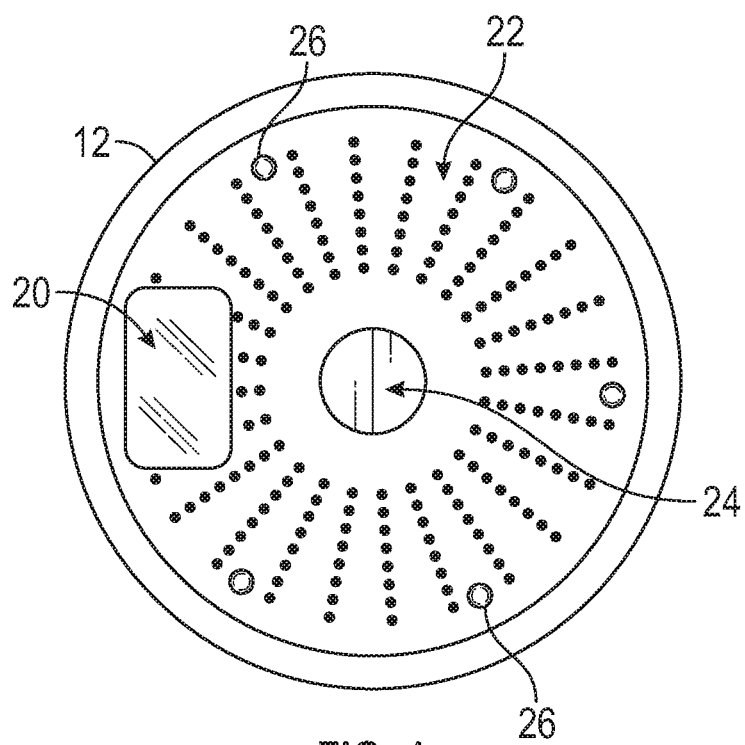
FIG. 4 shows a side elevational view of a component of a device for remotely monitoring the health of an animal in accordance with the present disclosure.

When the device is fitted to the ear 50 an animal such as a pig 68, as shown in FIG. 5, the post 40 extends through an opening in the ear 50 of the animal 68. The post 40 is sized so that a portion of the ear 50 fits between the first end of the post 40 and the disc 30 such that one side of the ear 50 contacts an inner facing surface 22 of the sensor housing 12 and an opposite side of the ear 50 contacts an inner facing 32 surface of the disc 30. In a preferred embodiment, as shown in FIGS. 3 and 4, the inner facing surfaces 22 and 32 are textured surfaces. The textured surface helps to prevent the device from sliding or rotating position once fitted to the animal's ear and also helps to provide ventilation for the surface of the ear covered by the device. In addition, as best seen in FIGS. 3 and 4, the inner facing surfaces 22 and 32 may also have bumps 26 spaced throughout the surfaces that are larger than relatively small projections that form the textured surface surrounding the bumps 26.

As shown in FIG. 3, the sensor housing 12 supports a heart rate sensor 72 positioned to measure a heart rate of the animal 68. In alternative embodiments, the device may include a temperature gauge. The temperature gauge may take the place of the heart rate sensor 72, or may be added to the device. The temperature gauge is preferably a digital thermometer. The heart rate sensor 72 is preferably an electro-optical heart rate sensor that shines light on the skin of the animal's ear 50 to detect changes in blood flow that occur with each heartbeat. The sensor housing 12 has a transparent window 20 positioned directly adjacent to the ear 50 of the animal through which the sensor 72 directs light to detect heart rate. In alternative embodiments, the sensor housing 12 may utilize a temperature gauge or thermometer 20 in place of a transparent window. When the device 10 is secured to the ear 50 of an animal 68, the spring 38 causes the disc 30 to be biased toward the animal's ear 50, thereby ensuring a snug fit to the ear at all times. As the animal grows and the ear 50 becomes thicker, the spring 38 may compress further, thereby maintaining a snug fit. Thus, the device 10 may be fitted to the ear 50 of a newborn piglet and may remain in place for the life of the pig 68, during which time the ear 50 may become thicker as the animal grows. Although the device 10 is preferably utilized with pigs 68, it should be understood that the device may be fitted onto the ear of other types of animals. In addition, the post 40 and the spring 38 may be sized and adapted for use on ears of varying thickness depending on the type of animal to which the device is fitted and may accommodate animal growth without requiring changing or adjusting the device.

The textured surfaces and bumps 26 on the inner facing surfaces 22 and 32 of the device 10 prevent the device from rotating when fitted onto the ear 50, which maintains the position of the window 20 relative to a desired position on the ear 50, which is preferably adjacent to an auricular vein 52, as shown in FIG. 5. Thus, the texturing on the inner facing surfaces 22 and 32 in combination with the spring 38 keep the inner facing surfaces of the disc 30 and the sensor housing 12 in direct contact with the ear 50 and also maintain proper positioning on the ear so that the device 10 may obtain consistent, accurate heart rate readings.

A shown in FIG. 3, the heart rate sensor 72 is positioned so that the sensor can direct light through the transparent window 20 and onto the surface of the animal's ear 50. The sensor 72 is preferably an electro-optical sensor that utilizes the method of photoplethysmography (PPG), which illuminates the skin and then measures changes in light absorption. The sensor 72 generally comprises an optical emitter that sends light waves into the skin and a digital signal processor that captures refracted light and converts those signals into heart rate data. The optical emitter may comprise one or more LED lights and may utilize infrared light, or alternatively may utilize red, green, or blue light, or multiple light wavelengths. The heart rate sensor 72 is preferably configured to also function as a thermometer and an oximeter. Thus, the sensor 72 may obtain data relating to heart rate, body temperature, and oxygen saturation in the blood of the animal.

As shown in FIG. 3, in a preferred embodiment, the device 10 further comprises an accelerometer 74 that provides data relating to the motion of the animal, which provides an indication of the activity level of the animal. Preferably, the heart rate sensor 72 and accelerometer 74 are electronically connected to a multi-layer circuit board 70 that is attached to an inside surface of the outer case 14 of the sensor housing 12. The device may also comprise a microprocessor 76 for processing data. The device 10 further comprises a wireless data transmission system 80 configured to wirelessly transmit data recorded by the heart rate sensor 72 and the accelerometer 74 to a remote monitor 64 at defined time intervals. The wireless data transmission system 80 preferably utilizes Bluetooth Low Energy (BLE), RFID, or a similar wireless personal area network technology and comprises an antenna configured to transmit data. As shown in FIG. 3, these components as well as the battery 78 are preferably housed within the sensor housing 12, though in alternative embodiments, one or more of these components may be located on the exterior of the housing 12 or disc 30.

The device 10 may be secured to the ear 50 of an animal 68, as shown in FIG. 5, utilizing a standard ear tag applicator generally used for attaching ear tags to animals. To secure the device to the ear, the applicator may be used to puncture a hole through the ear 50 with the pointed cap 44 at the end of the post 40 before the disc 30 or the spring 38 are installed. Once the post 40 has been inserted through the formed opening in the ear 50 and is secured to the sensor housing 12, the disc 30 may then be installed by inserting the cap 44 through the opening 35 in the disc 30. The material of construction of the disc 30, as well as the sensor housing 12, preferably comprises polypropylene, polyurethane, or a similar type of plastic material, which may an antibacterial plastic to prevent infection when fitting the device onto an animal. The diameter of the opening 35 in the disc 30 is slightly smaller than the diameter of the cap 44 and slightly larger than the diameter of the post 40, which allows the disc 30 to slide along the post 40 when installed. The material forming the disc 30 is generally rigid but has a small amount of flexibility, which allows the disc 30 to be snapped into place over the cap 44. Once installed, however, the cap 44 will prevent the disc 30 from being removed from the post 40 without the application of force to remove the disc. After the disc 30 is installed, the spring 38 may then be installed by inserting the cap 44 through the coils of the spring 38. The spring is sized so that it has an internal coil diameter that is slightly smaller than the diameter of the cap 44 and slightly larger than the diameter of the post 40. The larger diameter of the cap 44 keeps the spring in place due to the spring 38 contacting a bottom surface of the cap around a circumference of the cap 44, as shown in FIG. 3. The opposite end of the spring 38 contacts the disc 30 so that the disc is biased away from the cap 44 and toward the first end of the post 40. Thus, as the animal grows and the ear 50 becomes thicker, the disc 30 will cause the spring 38 to further compress while maintaining pressure on the ear to keep a tight fit, which enables consistent and accurate data readings from the ear.

Alternatively, the device may be fitted onto an ear by inserting the first end of the post 40 through an opening in the ear 50 and then threading the first end of the post into the hole 24 in the sensor housing 12. The device may be removed from an ear by forcibly removing the spring 38 and the disc 30 over the cap 44 or, alternatively, by detaching the sensor housing 12 from the post 40.

In another aspect, a system for remotely monitoring animal health of a plurality of animals is provided, as best seen in FIG. 6. The system comprises a plurality of monitoring devices 10 each fitted onto the ear 50 of an individual animal 68, at least one aggregator 62, and a remote monitor 64 configured to wirelessly receive and display data related to specific individual animals within a group. Preferably, as shown in FIG. 6, a plurality of aggregators 62 are positioned around a pen, barn, or similar type of animal enclosure 60 and aggregate data received from the plurality of devices 10 fitted onto the animals 68 within the enclosure 60. The aggregators 62 are connected to a network to which a remote monitor 64 is connected so that a user may remotely monitor the health of all animals fitted with monitoring devices 10.

Each aggregator 62 comprises a central processing unit (CPU) and an antenna configured to wirelessly receive data from each of the individual devices 10 fitted onto each animal 68. The aggregators 62 are configured to receive data from the devices 10 at defined time intervals, which may be adjusted to collect data as frequently as desired. The aggregators 62 group and process data related to individual animals 68, which may be sorted and viewed on the monitor 64. The aggregators 62 are connected to the monitor 64 via a network, which is preferably a wireless local area network (LAN) but may include one or more wired or wireless networks of any kind such as an intranet, the Internet, another type of network, or a combination of networks. Animal health data is regularly transmitted from the aggregators 62 to the monitor 64 via the network. Alternatively, data may be transferred directly from the devices 10 to the monitor 64. Thus, the monitor 64 is configured to wirelessly receive animal health data either directly or via one or more aggregators 62. Aggregators 62 are preferably utilized to cover a wide area of an enclosure 60 or other areas where animals 68 may move to within a facility.

The remote monitor 64 is a computing device, which is preferably a mobile computing device that allows remote monitoring of data by a user from any location. The monitor 64 may include a smartphone, a tablet computer, a personal digital assistant, a laptop, desktop, workstation, or other computing device or monitor suitable for viewing and sorting data. The computing device may include a processor, a memory, a storage device, a high-speed interface connecting to a memory and high-speed expansion ports, and a low-speed interface connecting to a low-speed expansion port and a storage device. These components may be interconnected using various buses, and may be mounted on a common motherboard or in other manners as appropriate.

As shown in FIG. 6, the remote monitor 64 may be connected to a cloud network 66. All collected data is preferably transmitted to the cloud 66 for warehousing, processing, analysis, and reporting. Alternatively, the aggregators 62 may be connected directly to the cloud 66 and may transmit data directly to the cloud. The monitor 64 may also download data from the cloud 66.

The remote monitor 64 may be used to observe data relating to individual animals 68. The animal health data may include heart rate data, body temperature data, oxygen saturation data, and/or motion or activity data. The data is tracked over time so that trends may be observed. This data may be collected and used to directly monitor the health of the animal. In addition, this data may be used in an algorithm to calculate a metric relating to a hydration level of the animal 68, which may allow a user to monitor and identify animals needing treatment for dehydration. A software application installed on the monitoring device 64 may allow a user to sort data. For instance, a user may be able to view average data for a group of animals or select an individual animal and view all available data for that animal over a specified time period or at a current time. Thus, the system provides gapless information on an animal's health throughout the lifespan of the animal. The system may produce standard reports for a group of animals that a user may review. The user may additionally query a database in which the data is stored in order to create a custom report.

In a preferred embodiment, as shown in FIG. 1, the disc 30 of the device 10 has an outer surface 34 displaying a barcode 36. When the device is secured to the ear 50 of an animal, the barcode 36 is on the exterior side of the ear so that it easily visible. The barcode 36 provides a link to secondary data related to the specific individual animal 68 to which the device 10 is fitted. For instance, the barcode 36 may be linked to data relating to genetic information of the animal, vaccination history, illness history, feed history, and/or barn, crate, or pen history. When the device 10 is first fitted to an animal 68, the barcode 36 may be scanned by a scanner to associate a particular device 10 with a particular animal 68. Once this association is made, a profile for the animal may be updated each time a change occurs. For instance, when the animal receives a vaccination, the profile may be updated with the type and date of vaccination. When a user is viewing health data on a particular animal, this secondary data will also be available to the user by viewing the animal profile. To view data relating to a specific animal, user may select an individual animal 68 from a list of all animals in the system and view all data recorded and/or calculated based on data received from the heart rate monitor 72 and the accelerometer 74, as well as any secondary data contained in the animal profile that has been recorded and associated with the animal by scanning the barcode 36.

In a preferred embodiment, the system further comprises an alert system adapted to alert a user when a defined health parameter of an individual animal 68 falls outside predefined limits. These health parameters may related to the animal's heart rate, perspiration, exercise habits, eating and drinking habits, sleeping habits, and other similar health characteristics. The user may receive an alert on the monitor 64, which may be a smartphone or tablet computer that the user carries in his or her person. In other embodiments, the monitor may be a personal computer, designated workstation, or other suitable type of computing device capable of receiving an alert. The alert may be delivered as a specialized notification on a smartphone, tablet, or personal computer, or may be delivered by an email, text message, or similar type of notification method. For instance, if the heart rate, body temperature, or oxygen saturation level of the animal falls outside a defined range of values, the user may receive an alert that identifies the particular animal 68 and may additionally provide geolocation data to assist in locating the animal. Similarly, if the accelerometer detects an unusual activity level, including either excessive activity or limited activity, that falls outside a defined range, the user may again receive an alert. The user may also receive an alert if other data values such as a dehydration metric fall outside a defined range. The system may also calculate an estrus metric utilizing data recorded by the heart rate sensor and the accelerometer. The metric may utilize inputs such as heart rate, body temperature, and/or activity level to determine when a sow is in estrus and should be inseminated. The user may additionally receive an alert indicating an ideal insemination time based on an estrus metric. In addition, the system may be configured to provide alerts to the user based on secondary data associated with a profile of a particular animal. For instance, if the animal needs a vaccination or a follow-up inspection at a certain time based on past medical or vaccination history, a notification may be sent to the user.

In a preferred embodiment, each device 10 fitted onto an animal 68 further comprises an alert light that is operatively connected to the alert system such that the alert light is activated by the alert system when the user receives an alert indicating that a health parameter of an individual animal has fallen outside predefined limits. The light allows the user to easily identify the animal requiring attention when the animal is in a large group. In a preferred embodiment, the light is housed within the sensor housing 12 and the sensor housing is made of a translucent material so that the housing is illuminated when light is activated. In alternative embodiments, the light may be located on the exterior of the sensor housing 12 or the disc 30.

The sensor housing 12, the post 40, the disc 30, and the battery 78 of the device are disposable. The circuit board 70 and other components, including the heart rate monitor 72, temperature gauge or thermometer, the accelerometer 74, the wireless transmission system 80 including antenna, and the microprocessor 76 may be reused on multiple animals 68. Once the device 10 has been removed from an animal, the inner case 16 may be unscrewed from the outer case 14 and the various components inside the sensor housing 12 may be removed and reinstalled in a new unit. A new profile for a new animal will be created within the system. New information relating to the new animal may then be input into the profile by the user, and the profile may be associated with the new animal via a new barcode 36 located on the disc 30 of a new unit.

In an alternative embodiment, the sensor housing 12 may comprise a band that has a pocket or pouch located within the band to hold the heart rate sensor 72, battery 78, and other components housed within the sensor housing 12. The band has a transparent window on an inside portion of the band for directing light from the heart rate sensor onto the ear of the animal. In this embodiment, the first end of the post is attached to the band, and the band hangs downward from the first end of the post. This embodiment may be advantageous in distributing the weight of the components of the device such as the heart rate sensor and battery. Preferably, the band has a second end having an opening therein, and the cap 44 of the post 40 is inserted through the opening so that the second end of the band is secured to the post. In this configuration, the band is preferably made of an elastic material and extends downward below the ear of the animal and is wrapped around the ear in order to fit snugly around the ear to provide consistent and accurate readings of the heart rate monitor.

The methods shown and described above are exemplary. Though certain characteristics of the present inventions are described above, the description is illustrative only. It is understood that versions of the invention may come in different forms and embodiments. Additionally, it is understood that one of skill in the art would appreciate these various forms and embodiments as falling within the scope of the invention as disclosed herein.

What is claimed is:

1. A device for remotely monitoring animal health, wherein the device is configured to secure to an ear of an animal to be monitored, said device comprising:
    a sensor housing;
    a post attached to the sensor housing at a first end of the post, wherein the post extends outwardly from the sensor housing;
    a disc having an opening extending through the disc and sized to receive the post therethrough such that the disc is slidably secured to the post;
    a cap secured to a second end of the post opposite the first end; and
    a spring positioned around the post and disposed between the disc and the cap such that the disc is biased toward the first end of the post,
    wherein the post is sized such that a portion of the ear of the animal to be monitored fits between the first end of the post and the disc such that one side of the ear contacts an inner facing surface of the sensor housing and an opposite side of the ear contacts an inner facing surface of the disc when the device is secured to the ear with the post inserted through an opening in the ear of the animal, and wherein the sensor housing supports at least one sensor to measure a health parameter of the animal when the device is secured to the ear of the animal, and wherein the device further comprises a power source and a wireless data transmission system configured to wirelessly transmit data recorded by the sensor to a remote monitor at defined time intervals.

2. The device of claim 1, said sensor being a temperature gauge.

3. The device of claim 1, said sensor being a heart rate monitor.

4. The device of claim 3, further comprising an accelerometer.

5. The device of claim 3, wherein the heart rate monitor is an electro-optical heart rate sensor, wherein the sensor housing has a transparent window through which the heart rate sensor shines light to contact a surface of the ear, wherein the window is positioned directly adjacent to the ear of the animal.

6. The device of claim 1, further comprising an accelerometer.

7. The device of claim 1, further comprising an alert light adapted to be activated when a health parameter of the animal falls outside predefined limits.

8. The device of claim 1, wherein the disc has an outer surface that displays a barcode linked to secondary data related to a specific individual animal.

9. The device of claim 1, wherein the inner facing surface of the disc and the inner facing surface of the sensor housing are textured surfaces.

10. A system for remotely monitoring animal health, said system comprising a plurality of monitoring devices, at least one aggregator, and a remote monitor configured to wirelessly receive and display data related to specific individual animals within a plurality of animals, wherein each monitoring device is configured to secure to an ear of an animal to be monitored, wherein each monitoring device comprises:
  a sensor housing;
  a post attached to the sensor housing at a first end of the post, wherein the post extends outwardly from the sensor housing;
  a disc having an opening extending through the disc and sized to receive the post therethrough such that the disc is slidably secured to the post;
  a cap secured to a second end of the post opposite the first end; and
  a spring positioned around the post and disposed between the disc and the cap such that the disc is biased toward the first end of the post,
  wherein the post is sized such that a portion of the ear of the animal to be monitored fits between the first end of the post and the disc such that one side of the ear contacts an inner facing surface of the sensor housing and an opposite side of the ear contacts an inner facing surface of the disc when the monitoring device is secured to the ear with the post inserted through an opening in the ear of the animal, and
  wherein the sensor housing supports a sensor positioned to measure a health parameter of the animal when the monitoring device is secured to the ear of the animal, and
  wherein the monitoring device further comprises a power source and a wireless data transmission system configured to wirelessly transmit data recorded by the sensor to the at least one aggregator at defined time intervals.

11. The system of claim 10, wherein each monitoring device further comprises an accelerometer.

12. The system of claim 10, wherein the sensor is an electro-optical heart rate sensor, wherein the sensor housing has a transparent window through which the heart rate sensor shines light to contact a surface of the ear, wherein the window is positioned directly adjacent to the ear of the animal.

13. The system of claim 10, further comprising an alert system adapted to alert a user when a health parameter of one of the individual animals within the plurality of animals falls outside predefined limits.

14. The system of claim 13, wherein each monitoring device further comprises an alert light operably connected to the alert system such that the alert light is activated by the alert system when a health parameter of one of the individual animals within the plurality of animals falls outside predefined limits.

15. The system of claim 10, wherein the disc of each monitoring device has an outer surface that displays a barcode linked to secondary data related to one of the individual animals within the plurality of animals.

16. The system of claim 10, wherein the inner facing surface of the disc and the inner facing surface of the sensor housing of each monitoring device are textured surfaces.

17. A method for remotely monitoring the health of an animal,
  said method comprising the steps of:
  securing a monitoring device to an ear of an animal to be monitored, wherein the monitoring device comprises:
    a sensor housing;
    a post attached to the sensor housing at a first end of the post, wherein the post extends outwardly from the sensor housing;
    a disc having an opening extending through the disc and sized to receive the post therethrough such that the disc is slidably secured to the post;
    a cap secured to a second end of the post opposite the first end; and
    a spring positioned around the post and disposed between the disc and the cap such that the disc is biased toward the first end of the post,
    wherein the post is sized such that a portion of the ear of the animal to be monitored fits between the first end of the post and the disc such that one side of the ear contacts an inner facing surface of the sensor housing and an opposite side of the ear contacts an inner facing surface of the disc when the monitoring device is secured to the ear with the post inserted through an opening in the ear of the animal, and
    wherein the sensor housing supports a sensor positioned to measure a health parameter of the animal when the monitoring device is secured to the ear of the animal, and
    wherein the monitoring device further comprises a power source and a wireless data transmission system configured to wirelessly transmit data recorded by the sensor to a remote monitor at defined time intervals;
  wirelessly connecting the monitoring device to the remote monitor; and
  transmitting data from the monitoring device to the remote monitor at defined time intervals.

18. The method of claim 17, wherein the monitoring device further comprises an accelerometer.

19. The method of claim 17, wherein the sensor is an electro-optical heart rate sensor, wherein the sensor housing has a transparent window through which the heart rate sensor shines light to contact a surface of the ear, wherein the window is positioned directly adjacent to the ear of the animal.

20. The method of claim 19, wherein the monitoring device is operably connected to an alert system adapted to alert a user when a health parameter of one of the individual animals within the plurality of animals falls outside predefined limits, further comprising the step of alerting a user when a health parameter of one of the individual animals within the plurality of animals falls outside predefined limits.

21. The method of claim 20, wherein the monitoring device further comprises an alert light operably connected to the alert system such that the alert light is activated by the alert system when a health parameter of the animal falls outside predefined limits, further comprising the step of activating the alert light when a health parameter of the animal falls outside predefined limits.

22. The method of claim 17, wherein the disc of the monitoring device has an outer surface that displays a barcode linked to secondary data related to a specific individual animal.

23. The method of claim 17, wherein the inner facing surface of the disc and the inner facing surface of the sensor housing are textured surfaces.

\* \* \* \* \*